United States Patent [19]
Rubin et al.

[11] Patent Number: 5,888,705
[45] Date of Patent: Mar. 30, 1999

[54] COMPOSITIONS AND METHOD OF STIMULATING THE PROLIFERATION AND DIFFERENTIATION OF HUMAN FETAL AND ADULT PANCREATIC CELLS EX VIVO

[75] Inventors: Jeffrey Rubin, Rockville, Md.; Alberto Hayek, La Jolla; Gillian Marguerite Beattie, Poway, both of Calif.; Timo Pyry Juhani Otonkoski, Helsinki, Finland; Vito Quaranta, La Jolla, Calif.

[73] Assignees: The United States of America as represented by the Department of Health and Human Services, Washington, D.C.; The Whittier Institute for Diabetes and Endocrinology, La Jolla, Calif.

[21] Appl. No.: 732,230

[22] PCT Filed: Apr. 28, 1995

[86] PCT No.: PCT/US95/05521

§ 371 Date: Apr. 14, 1997

§ 102(e) Date: Apr. 14, 1997

[87] PCT Pub. No.: WO95/29989

PCT Pub. Date: Nov. 9, 1995

Related U.S. Application Data

[63] Continuation-in-part of Ser. No. 235,394, Apr. 29, 1994, Pat. No. 5,587,309.

[51] Int. Cl.[6] ............................ A01N 1/02; C12N 5/08; C07K 16/24; A61K 38/19
[52] U.S. Cl. .................... 435/366; 424/93.7; 435/1.3; 435/471; 435/380; 435/402; 435/405; 435/406; 530/388.23; 530/399

[58] Field of Search ..................... 435/402, 405, 435/371, 380, 1.3, 810, 406, 366; 530/399, 388.23; 424/556, 562, 931, 93.7

[56] References Cited

U.S. PATENT DOCUMENTS 5,510,263  4/1996  Quaranta et al. ................ 435/240.243
5,587,309  12/1996  Rubin et al. ......................... 435/240.2

OTHER PUBLICATIONS

Otonkoski, T et al. J. Clin. Invest. 92: 1459–1466, Sep. 1993.

Kneteman, NM et al. Diabetes. 38(3): 386–396, Mar. 1989.

*Primary Examiner*—David Saunders
*Assistant Examiner*—F. Pierre VanderVegt
*Attorney, Agent, or Firm*—Needle & Rosenberg, P.C.

[57] ABSTRACT

A method of inducing the proliferation and/or differentiation of human adult pancreatic cells entails contacting primary cultures of such cells with Hepatocyte Growth Factor/Scatter Factor (HGF/SF), thereby inducing a proliferation of β-epithelial cells, an increase in the number of β-epithelial cells which form islet-like cell clusters, and an increase in insulin production per cell. The method is improved by culturing the cells on an extracellular matrix such as 804G in the presence of HGF/SF, and is further improved by reaggregating thus-treated cells and contacting said cells with an insulin gene upregulating agent such as a poly(ADP-ribose) synthetase inhibitor such as a nicotinamide or benzamide. The method provides increased numbers of functional islet-like cell clusters for transplantation.

25 Claims, 10 Drawing Sheets

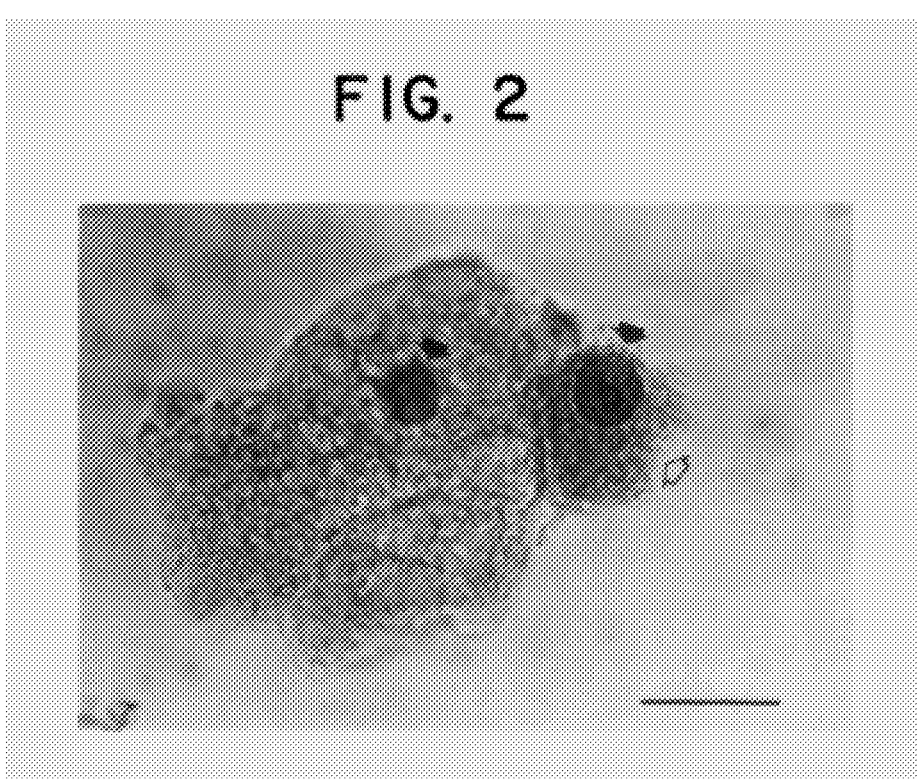

COMPOSITIONS AND METHOD OF STIMULATING THE PROLIFERATION AND DIFFERENTIATION OF HUMAN FETAL AND ADULT PANCREATIC CELLS EX VIVO

This application is a 371 of PCT/US95/05521, filed Apr. 28, 1995, which is a continuation-in-part of application Ser. No. 08/235,394, filed Apr. 29, 1994, now U.S. Pat. No. 5,587,309.

BACKGROUND OF THE INVENTION

The present invention relates to transplantation of human fetal or mature pancreatic cells to treat Type 1 diabetes mellitus. More particularly, the invention relates to the use of a human cytokine, hepatocyte growth factor/scatter factor ("HGF/SF"), to induce ex vivo the proliferation and differentiation of pancreatic cells prior to their transplantation into a diabetic subject.

Type 1 (insulin-dependent) diabetes mellitus is characterized, inter alia, by a loss of insulin-producing Beta ("β") cells and decompensation of metabolism following autoimmune aggression. Fisenharth, *N. Eng. J. Med.* 314: 1360 (1986); Sweane, *Diabetologia* 35: 193 (1992). Treatments of such patients have included primarily parenteral administration of bovine or porcine insulin or recombinant human insulin. This treatment, however, delays, but does not avoid, the pathological sequelae of this disease, and, in addition, requires multiple daily injections of insulin and/or the use of an indwelling catheter and an insulin pump.

Immunosuppressive treatment of patients, for example, with cyclosporin A or FK506, also has been effected, but with only limited success, on a theory that Type 1 diabetes mellitus is a disease of autoaggression. Immunosuppressive drugs have toxic side effects, including the potential for infection as the result of suppression of the immune system.

Recently, adult human pancreatic islets have been transplanted into patients in order to achieve independence from insulin injections. Scharp et al., *Transplant.* 51: 76 (1991); Warnock et al., *Diabetologia* 34: 55 (1991). Despite these advances, the limited number of organ donors, the inadequate islet masses obtainable from most mature pancreases, and graft rejection problems have conspired to limit the general usefulness of this approach. Ricordi et al., *Transplant.* 53: 407 (1992).

An alternate source of pancreatic islets for 5 transplantation is the fetal pancreas. This tissue is rich in undifferentiated β-cells that can, at least in theory, grow and mature after transplantation. Tuch et al., *Diabetes* 35: 464 (1986). While the immature immune system of the fetus reduces the likelihood of fetal islet rejection by the recipient, problems relating to the limited availability of suitable fetal pancreases and to the immaturity of the insulin-producing cells in such tissues continue to hinder success in this approach. For a review, see Andersson, *Transplantation Revs.* 6: 20 (1992).

HGF, a 87 kDa two-chain glycoprotein cytokine first identified in rodent and human plasma and rodent blood platelets, is a potent hepatocyte mitogen. Rubin et al., *Biochem. Biophys. Acta* 1155: 357 (1993). HGF is apparently identical to a fibroblast secretory protein referred to as Scatter Factor ("SF") known to dissociate and increase the motility of epithelial cells. Gherardi et al., *Nature* 346: 228 (1990); Weidner et al., *Proc. Nat'l. Acad. Sci.* (USA) 88: 7001 (1991); Furlong et al., *J. Cell Sci.* 100: 173 (1991); Naldini et al., *EMBO J.* 10: 2867 (1991); Bhargava et al., *Cell Growth Differ.* 3: 11 (1992). For this reason, "HGF/SF" is used here as the abbreviation of the name of this cytokine.

For reviews of the biology of HGF/SF, see Strain, *J. Endocrinol.* 137: 1 (1993), Furlong, *BioEssays* 14: 613 (1992), and Rubin et al. (1993), above.

HGF has been purified to homogeneity and sequenced, and its gene has been cloned. See Miyazawa et al., *Biochem. Biophys. Res. Commun.* 163: 967 (1989); Rubin et al., *Proc. Nat'l Acad. USA* 88: 415 (1991); Weidner et al., *Sci.* (USA) 88: 7001 (1991); Nakamura et al., *FEBS Lett.* 224: 311 (1987); Nakamura et al., *Nature* 342: 440 (1989) Gohda et al., *J. Clin. Invest.* 81: 414 (1988).

Wolf et al., *Hepatology* 14: 488 (1991), identified HGF/SF in adult human pancreatic tissue by immunohistochemistry. However, the identifying signal was strong only in exocrine tissue, very weak in endocrine tissues, with no apparent differences between various cell types. In sharp contrast, Tsuda et al., *Jpn. J. Cancer Res.* 83: 1262 (1992), reported immunohistochemistry studies that identified HGF/SF in adult (human and rat) pancreatic, glucagon-producing A cells, but not in the exocrine pancreas. The authors concluded that this cytokine is primarily produced or stored in the A cells, and it was hypothesized that HGF/SF may act as a growth factor in a paracrine and an endocrine fashion. Yet, DeFrances et al., *Development.* 116: 387 (1992), demonstrated immunohistochemically the presence of HGF/SF in developing rat fetal pancreas with intense staining in acinar cells.

The need persists, therefore, for a means of providing clinically useful numbers of higly proliferating and differentiating islet-like clusters of fetal and mature human pancreatic cells. This need has been met by the invention described below.

SUMMARY OF THE INVENTION

It is an object of this invention to provide a method for stimulating the proliferation of human pancreatic β-cells by treating primary cultures of fetal or adult pancreatic tissue with HGF/SF.

It is another object of this invention to provide a method for producing β-epithelial cell-containing islet-like cell clusters from primary cultures of human fetal and mature pancreatic cells by treating such cultures with HGF/SF.

It is yet another object of this invention to provide a method for increasing insulin production in primary cultures of human pancreatic cells by treating such cells with HGF/SF.

It is still another object of this invention to provide a method of preparing quantities of HGF/SF-treated functional human fetal and mature pancreatic β-islet cells in amounts sufficient for transplantation into diabetic patients.

A method for stimulating the ex vivo proliferation and differentiation of human pancreatic β-islet cells, comprising the steps of:

(a) preparing a primary culture of said human pancreatic cells; and, (b) contacting said primary culture cells with an effective concentration of HGF/SF, and optionally with an effective concentration of anti-TGF-β antibodies, for an effective period.

It is also an object to provide a method of ex vivo expansion of human pancreatic cells by growth on a specific extracellular matrix in the presence of HGF/SF. Subsequent reaggregation of cells from monolayer culture and treatment with a poly(ADP-ribose) synthetase inhibitor increases expression of islet-specific genes (such as insulin).

These and other aspects of the invention will become apparent by reference to the following detailed description of the invention and the appended claims.

BRIEF DESCRIPTION OF THE DRAWINGS

FIG. 2 shows a demonstration of β-islet cell replication in HGF/SF-treated ICCs by double immunostaining for BrdU (black arrows) and insulin (open arrows) which detects cells positive for both antigens.

DETAILED DESCRIPTION OF THE PREFERRED EMBODIMENTS

Figure 1A:
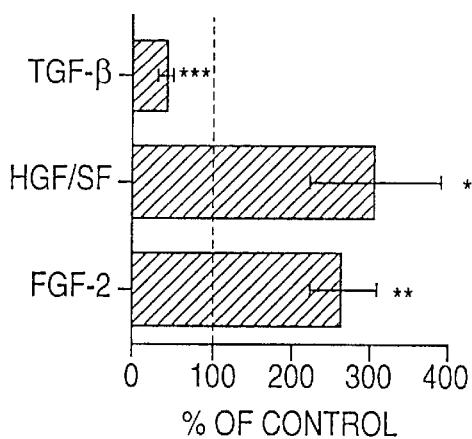
FIGS. 1A–1D show a histogram showing the differential effects of HGF/SF, TGF-β and FGF-2 on the yield from human fetal pancreatic cell cultures of islet-like cell clusters (FIG. 1A), of total DNA (FIG. 1B), of total insulin content (FIG. 1C), and of insulin content per unit of DNA content (FIG. 1D).
Figure 1B:
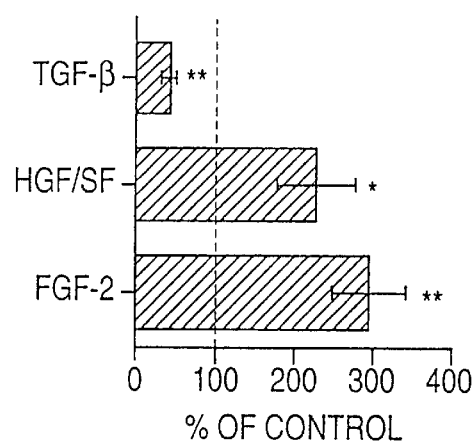
Figure 1C:
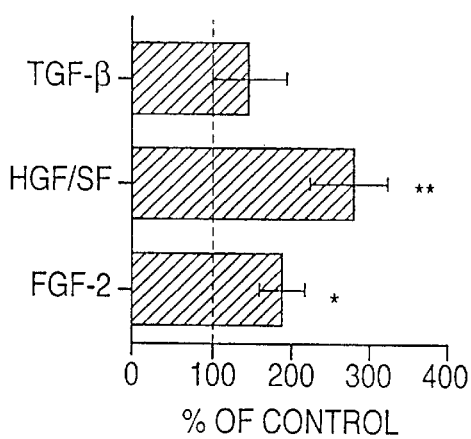
Figure 1D:
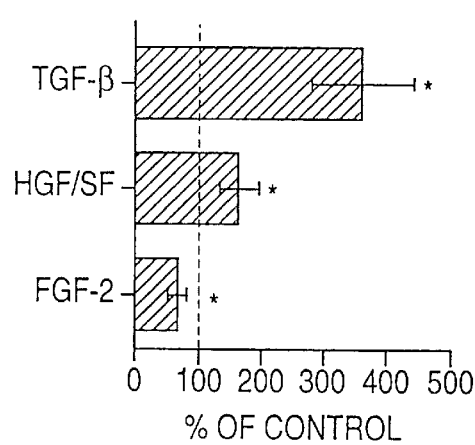

It has been discovered that primary cultures of human pancreatic cells unexpectedly can be induced to proliferate and to differentiate, that is, to produce increased numbers of pancreatic cells that form islet-like cell clusters ("ICC") containing a high percentage of β-epithelial cells with increased insulin production, by culturing the primary culture cells ex vivo with an effective concentration of the cytokine HGF/SF for an effective period of time under appropriate growth conditions. Proliferating, differentiated ICCs prepared in this manner can be used for transplantation into diabetic subjects, particularly into Type 1 diabetic human patients in whom insulin production is compromised in order to alleviate the symptoms of the disease, as well as into animal models of diabetes for the development of human treatment modalities.

The present data demonstrate clearly that the method of the invention can be applied, not only to human fetal pancreatic cells, but also to mature (e.g., adult) human pancreatic cells. Nevertheless, the former are highly preferred because: (a) the immature immune system of the fetus reduces the likelihood of fetal islet rejection; and (b) the proliferative and differentiation response of fetal pancreatic cells to HGF/SF and other factors exceeds that observed with adult cells.

Expanding such treated pancreatic cultures increases the supply of functional β-cell islets for transplantation into diabetic subjects in clinically useful numbers.

"Primary culture" denotes a mixed cell population of human pancreatic cells that permits interaction of epithelial and mesenchymal cells within ICC. The word "primary" takes its usual meaning in the art of tissue culture.

By "ex vivo" is meant cells that have been taken from a body, temporarily cultured in vitro, and returned to a body.

"Proliferation" indicates an increase in cell number.

"Differentiation" in the present context means increased numbers of islet-like cell clusters containing an increased proportion of β-epithelial cells that produce increased amounts of insulin.

"HGF/SF" is the abbreviation for hepatocyte growth factor/scatter factor. An "effective concentration" of HGF/SF is one that will induce primary cultures of human fetal pancreatic cells to proliferate, to form ICC, to increase the number of β-epithelial cells, and to increase insulin production. Preferred concentrations are 5 to 50 ng/ml, most preferred are 15 to 35 ng/ml growth medium. By "effective period" is meant the length of time necessary to observe the aforementioned enhancements.

"FGF-2" refers to basic fibroblast growth factor. "FGF-7" means keratinocyte growth factor. "IGF-I" and "IGF-II" refer to insulin-like growth factors. "TGF-β" means transforming growth factor β. "NGF" is the abbreviation for nerve growth factor. "EGF" means epidermal growth factor. "Ab-1" means monoclonal anti-IGF-1 receptor. "AB-101-NA" means chicken anti-human TGF-β.

By "extracellular matrix" is meant a complex mixture of macromolecules secreted by cells and located between and around such cells, and made insoluble by cross-linking. Generally, such matrices consist of collagen scaffolding to which various adhesive proteins, glycosaminoglycans, sulfated heparins and proteoglycans are bound.

Pancreatic Tissue Source

Human fetal pancreases can be obtained at various gestational periods (18 to 24 weeks are preferred) from a non-profit procurement source such as Advanced Bioscience Resource, Oakland, Calif., The International Institute for the Advancement of Medicine, Exton, Pa., and the Anatomic Gift Foundation, Laurel, Md., following IRB review and approval. Pancreases should be shipped on ice in a standard culture medium (e.g., RPMI-1640, Irvine Scientific, Irvine, Calif., supplemented with 10% normal human serum and antibiotics (penicillin 100 U/ml, streptomycin 0.1 mg/ml, and amphotericin B 1 mg/ml), and should be received within 18 to 24 h of harvesting.

Tissue Culture

Digestion and culture of pancreases is carried out conventionally, as described by Otonkoski et al., *Acta Endocrinol.* 118: 68 (1988). Briefly, fragments of the tissue are digested with collagenase, for example, collagenase P (product of Boehringer; Indianapolis, Ind.). After being washed in a balanced salt buffer solution, the digested tissue is plated on culture dishes of a type that discourages cell attachment in RPMI-1640 medium containing 10% human serum, such as diSPo (product of Baxter, McGraw Park, Ill.), and is cultured in a complete growth medium (e.g., RPMI-1640) supplemented with human serum and antibiotics.

Where multiple variables are to be examined, it is convenient to use sets of dishes, with one set serving as the control and the remainder serving to test various growth factors.

It is within the scope of this invention to expand cell yield so as to produce clinically useful, that is, bulk quantities, of islet cells for transplantation into patients or other uses by culturing pancreatic cells in a large bioreactor. By "bulk quantities" is meant numbers of cells suitable for transplantation into numbers of patients in order to relieve or ameliorate a disease condition.

In general, in such an expanded culture procedure a commercial-sized bioreactor, such as the OPTICAL™ culture system, Model 5300E (Charles River Labs.; Wilmington, Mass.), or the CELLMAX™ QUAD cell culture system (Cellco, Inc.; Germantown, Md.), is seeded with a primary culture of human pancreatic cells. The bioreactor is perfused with a suitable, complete growth medium supplemented with an appropriately effective concentration of HGF/SF, e.g., 10 ng/ml. The β-epithelial cell-containing islet-like clusters are then harvested. Cells may be cryopreserved prior to use as described, for example, by Beattie et al., *Transplantation* 56: 1340 (1993).

Monolayer Culture on Extracellular Matrix

While HGF/SF can induce potent mitogenic and differentiation effects in human pancreatic β-cells grown as three dimensional ICCs free floating in a culture medium, we have unexpectedly found that a combination of growing such cells as monolayers on certain extracellular matrices with treatment of such cultures with HGF/SF produces a synergistically increased mitogenic effect that is as much as 10-fold greater than observed with ICCs grown in the absence of matrix or growth factor. As much as a three-fold increase in mitogenic effect may be observed when cells are grown on a matrix compared to no matrix. ICCs generated from cells grown on extracellular matrices in combination with the growth factor also exhibit greatly increased epithelial and β-cell content. Growth of fetal or mature pancreatic cells as a monolayer culture on an extracellular matrix is a highly preferred method according to this invention.

It is also important that the synergistic effect of a combination of HGF/SF and extracellular matrix is not limited to fetal human pancreatic cells, but can be observed with mature human pancreatic cells (see example below), thereby providing an alternate source of tissue.

Preferred extracellular matrices are the well-known extracellular matrices from rat bladder carcinoma cell line 804G, see Langhofer et al., *J. Cell Science* 105:753 (1993), and BCEM bovine corneal endothelial cells, see Gospdarowicz et al., in Cell Culture: Methods For Molecular And Cell Biology, Barnes et al., eds., Alan R. Liss, N.Y., 1984, p.275–295). But other extracellular matrices exhibiting the functional properties of 804G and BCEM are within the scope of this invention. The matrices can be prepared as previously described, for example, by Hayek et al., *In Vitro* 25:146 (1989).

Although specific exemplification of the use of an extracellular matrix is provided below in the examples, generally, free floating ICCs are first prepared in petri dishes from pancreases as described above and in the examples. Selected ICCs of uniform size (generally, 50–70 μm in diameter) and homogeneous translucent appearance are hand-picked and plated in RPMI-1640 containing 10% human serum on culture dishes coated with an extracellular matrix. ICCs picked in this way are highly enriched in epithelial cells. At a selected time (typically after 5 days of growth), monolayer cells are removed from the matrix using non-enzymatic dissociating medium (Sigma Corp., St. Louis, Mo.), dispersed and washed as single cell suspensions, then reaggregated.

Fetal pancreatic cells may be induced to upregulate the insulin gene and thereby greatly increase insulin production by contacting these cells either as primary cultures, as monolayers on an extracellular matrix or as reaggregated monolayers cells with a biochemical agent that upregulates the insulin gene. It has been found that poly(ADP-ribose) synthetase inhibitors, such as a nicotinamide or a benzamide, typically at a concentration of about 10 mM, are highly preferred insulin gene upregulators according to the present invention. In this connection, it is of interest that nicotinamide alone, or together with insulin, has been studied as a treatment for Type I diabetes in humans and in animal models, with unclear results. See, e.g., Session on Nicotinamide In Diabetes, in *Nicotinamide: biological actions and therapeutic potential in diabetes prevention,* A workshop of the International Diabetes Immunotherapy Group, Copenhagen, Dec. 4–5, 1992, Abstracts. Other specific inhibitors of poly(ADP-ribose) synthetase are listed in Banasik et al., Specific Inhibitors of Poly(ADP-ribose) Synthetase, in Poirier et al., eds., *ADP-ribosylation reactions,* Tables 1–5, pp 344 et seq., Springer Verlag, New York, 1992.

Reaggregated monolayer cells may then be transferred to petri dishes, in preparation for transplantation of thus-expanded islet cell populations into a test animal model or a patient.

Islet Cell Transplantation

The treated pancreatic cells, particularly those that have been induced to form islet-like cell clusters, either freshly harvested or cryopreserved, can be placed in a suitable pharmaceutical vehicle for infusion into patients or experimental models of diabetes. For example, cells are washed with RPMI-1640 medium supplemented with 1 to 10% human serum albumin or with CMRL-1066 medium supplemented with 2 to 3% human serum albumin prior to suspension in a pharmaceutical vehicle. (See REMINGTON'S PHARMACEUTICAL SCIENCES for suitable suspension fluids.) Cells then are loaded into syringes, such as 60-ml syringes, for infusion into human patients. See, e.g., Scharp et al. (1991), Warnock et al. (1991), and Ricordi et al. (1992), all cited above. Suitable routes for infusion of cells into patients include intraportal, intrasplenic, renal subcapsular space and intravenous routes. The kidney route is preferred because it is a relatively immunoprivileged site, and implantation at this site may be less susceptible to endocrinological deterioration. Andersson et al., *Transplantation Revs.* 6: 20 (1992).

In Vitro Incubation Conditions

It is preferred to use 10% human serum with all growth factors except IGF-I, IGF-II or PDGF with which a supplement of 1% human serum, transferrin and bovine serum albumin (BSA) is preferred. The growth medium is changed at suitable intervals, preferably at about 3 days of incubation.

Where it is desired to measure the extent of cell proliferation, at a suitable time after plating, [methyl -$^3$H]-thymidine (Amersham; Arlington, Ill.) can be added to each culture vessel, and the increase in cellular radioactivity followed.

Rounded cell aggregates (ICC) can be picked and counted under a stereomicroscope. In order to collect cells for further analysis, these ICC's can be combined with the remaining cells in the dish (isolated by brief low speed centrifugation as described in the examples below). After washing the combined cells with a balanced salt buffer, (such as HBSS), the cells are sonicated, the DNA content measured, (for example, via the fluorometric approach described by Hinegarden, *Anal. Biochem.* 39: 192 (1971), and the insulin content measured conventionally, for example by RIA (DPC; Los Angeles, Calif.) on an ethanol extract of the cell sonicate. Incorporation of radioactive thymidine can be determined by liquid scintillation counting.

Bioactive Peptides and Antibodies

Recombinant human IGF-1 and IGF-II (100 ng/ml) may be obtained from The Whittier Program at the University of California at San Diego, La Jolla, Calif. 92037. Collaborative Research (Bedford, Mass.) is a source of recombinant human PDGF (10 ng/ml), 7s NGF (100 ng/ml), and mouse EGF (25 ng/ml). Recombinant human TGF-α (25 ng/ml) is a product of Sigma (St. Louis, Mo.).

Recombinant human HGF/SF (25 ng/ml) is produced by a baculovirus expression system as follows:

The insect cell line *Spodoptera frugiperda* (Sf9) was obtained from the American Type Culture Collection and grown at 27° C. in EXCELL 400 (JR Scientific) serum free growth medium. *Autographica californica* virus (AcNPV) can be obtained from Dr. M. Summers, Texas A&M University. Sf9 cells are infected with a multiplicity of infective particles of $\geq 10$ plaque-forming units/cell for protein expression studies and 0.1–10 pfu/cell for virus stock production. The baculotransfer vector pVL941 can be produced according to Luckow et al., *Virology* 170: 31 (1989). To insert human HGF/SF cDNA into pVL941, the full-length coding region of HGF/SF may be generated by polymerase chain reaction (PCR) using Bam Hi restriction enzyme-tagged oligonucleotide primers. PCR amplified product is cleaved with Bam H1 and subcloned into the Bam H1 site of the baculovirus vector pVL941. Recombinant baculovirus was produced by cotransfecting Sf9 insect cells with AcN-PVDNA (1 mg) and pVL-HGF (2 mg) by calcium phosphate transfection. The resulting culture supernatant fluids are harvested after 4 days, and screened for homologous recombination by visual inspection and dot-blot hybridization using a $^{32}$P-labeled, nick-translated HGF cDNA probe. Purified recombinant baculovirus may be obtained after 3 rounds of plaque purification. For the expression of recombinant HGF/SF, Sf9 cells were infected with the recombinant baculovirus grown in medium, such as EXCELL 400, for 3 days. The resulting conditioned medium is harvested, clarified by centrifugation at 1000×g for 10 mins., and stored frozen at –20° C. Subsequently, the medium is thawed, and concentrated by ultrafiltration (YM filter, 10 kDa cutoff, Amicon). The recombinant HGF/SF in the concentrate may be purified by heparin affinity chromatography essentially as previously described. Rubin et al., *Proc Nat'l Acad. Sci. USA* 88: 415 (1991).

Recombinant human FGF-2 (50 ng/ml) is made according to Isaachi et al., loc. cit. 88: 2628 (1991). Recombinant human KGF/FGF-7 (50 ng/ml) is produced according to Ron et al., *J. Biol. Chem.* 268: 2984 (1993).

Monoclonal anti-IGF-1 receptor (2 µg/ml) is obtained from Oncogene Science (Uniondale, N.Y.), and chicken anti-human TGF-β (5 µg/ml) from R & D Systems (Minneapolis, Minn.).

Immunohistochemistry and Morphometry

ICCs can be incubated with bromodeoxyuridine ("BrdU"), fixed in formaldehyde, embedded in paraffin and sectioned. Sections can be stained for insulin using an immunoalkaline phosphatase technique described, for exampole, by Erber et al., *Am. J. Clin. Path.* 88: 43 (1987), using polyclonal guinea pig anti-porcine insulin (Chemicon; El Sequndo, Calif.) as the primary antibody.

Cell nuclei that have incorporated BrdU during DNA synthesis can be identified using mouse monoclonal anti-BrdU (Dako; Carpintaria, Calif.), detected with the immunoperoxidase technique of Sternberger et al., *J. Histochem., Cytochem.* 18: 315 (1970), followed by hematoxylin counterstaining.

Epithelial cells can be identified on separate sections using a mouse monoclonal anti-epithelial antigen antibody (Ber-EP4, Dako, above) as the primary antibody.

Surface areas of insulin-positive and epithelial cells, calculated as percent of the total ICC area, can be quantified with a computerized image analyzer (American Innovision; San Diego, Calif.). The same method can be used for the determination of the BrdU labeling index. Cells positive for both insulin and BrdU may also be recorded in separate sections of the same samples after double staining of the two antigens.

Mean cell size can be calculated by the ratio of total ICC area to the number of nuclei.

Mean β-cell size can be estimated by measuring the surface area of individual insulin-positive cells.

A sufficient number of ICC sections (at least 15) and nuclei (at least 1000) should be analyzed for each sample to correct for biological and experimental variability of the samples.

It has been observed that the cytokine TGF-B, which may be present in ICCs themselves or in the commercial human serum used in the growth media, has a deleterious effect on the proliferation and differentiation of fetal pancreatic cells. This deleterious effect may be obviated by adding to culture media neutralizing concentrations of anti-TGF-β antibodies, as described in Example 4 below.

Kits

Within the scope of this invention are mercantile kits containing, in separate compartments, a cryopreserved, HGF/SF-treated expanded human pancreatic cell culture plus one or more additional components such as HGF/SF, extracellular matrix, an insulin gene upregulating agent such as a poly(ADP-ribose) synthetase inhibitor (e.g., nicotinamide), and a pharmaceutically acceptable vehicle in which to suspend the cells for work up and use in a subject.

The present invention is described further by reference to the following illustrative examples that should not in any way be construed as limiting the scope of the invention which is defined by the specification and appended claims.

EXAMPLE 1

Generation of ICCs

Pancreases were dissected free of surrounding tissue and cut into 4 equally sized pieces. Tissues were then blotted, weighed, and cut into small pieces (1 mm3), Fragments were digested for 15 mins. in a shaking water bath (37° C., 200 osci/min) in Hank's balanced salt solution ("HBSS") containing 5.5 mg/ml collagenase P. Digested tissues were washed twice in cold HBSS and plated (¼pancreas/dish) on 60 mm petri dishes of a type that encourages cell attachment, in RPMI 1640 with 10% HSA and antibiotics. One of the dishes served as the control, and growth factors were added to the others. As noted above, the human serum albumin content of the medium was reduced to 1% in the case of IGF-I, IGF-II or PDGF, and the medium supplemented with 10 μg/ml transferrin and 0.1% BSA. Medium (with the additions) was changed after 3 days.

On the 5th day, 0.5 μCi/ml of labeled thymidine (5.0 Ci/mmol.) was added to each dish. After a 16 hr incubation, all well-formed rounded cell aggregates (ICCs) were picked and counted as described above.

The average number of ICCs harvested from control cultures in 10% HSA was 13.4 per mg of starting tissue (Table 1). The yield of tissue was not affected by the gestational age. Based on an analysis of 383 pancreases, the mean weight of pancreas was 102 mg at 18 wk and 247 mg at 24 wk. This implies that in this age range the average yield of ICCs was 1400–3300 per pancreas. The yield was To collect total cells, ICCs were combined with the small cell pellet from the dish isolated by centrifugation at 800×g for 3 mins. After two washes in HBSS, the cells were homogenized by sonication. DNA was analyzed flurometrically (see above).

There were no significant differences in the average DNA content/ICC (mean of controls 34 ng per ICC). The total amount of DNA, as an estimate of total cell number, reflected well the results calculated from the ICC (Table 1). Total DNA synthesis, as measured by $^3$H-thymidine incorporation at the end of the culture period, paralleled the results obtained by ICC numbers and DNA content.

TABLE 1

Effect of growth factors on the yield, DNA content and insulin content of ICCs.

| Culture Conditions | N | Number of ICCs (per mg tissue) | DNA content (per mg tissue) | Insulin content (per mg tissue) | (per μg DNA) |
|---|---|---|---|---|---|
| 10% HS | 41 | 13.4 (11.3–15.4) (100%) | 409 ng (335–483) (100%) | 0.8 pmol (0.6–1.1) (100%) | 2.9 pmol (1.6–4.2) (100%) |
| FGF-2 50 ng/ml | 11 | 265 (160–371)** | 302 (200–404)** | 187 (120–254)* | 70 (44–97)* |
| FGF-7 50 ng/ml | 9 | 131 (113–150)** | 166 (107–224)* | 95 (68–122) | 54 (34–74)** |
| HGF/SF 25 ng/ml | 9 | 308 (113–503)* | 233 (120–346)* | 280 (178–381)** | 165 (100–230)* |
| TGF-α 25 ng/ml | 6 | 192 (94–289) | 150 (92–209) | 144 (68–220) | 95 (71–120) |
| EGF 25 ng/ml | 6 | 136 (82–190) | 137 (46–228) | 188 (51–383) | 120 (73–167) |
| TGF-β 10 ng/ml | 6 | 43 (26–61)*** | 44 (16–72)** | 147 (25–268) | 366 (150–571)* |
| NGF 100 ng/ml | 8 | 121 (88–155) | 107 (62–204) | 186 (40–353) | 145 (72–217) |
| 1% HS | 12 | 9.2 (6.9–11.2) (100%) | 323 ng (216–407) (100%) | 0.5 pmol (0.3–0.8) (100%) | 2.0 pmol (0.7–3.2) (100%) |
| IGF-I 100 ng/ml† | 7 | 148 (90–207) | 147 (87–209) | 174 (100–250)* | 127 (86–167) |
| IGF-II 100 ng/ml† | 7 | 155 (103–206)* | 135 (84–187) | 145 (91–197) | 115 (60–171) |
| PDGF 10 ng/ml† | 9 | 149 (78–219) | 147 (62–232) | 133 (44–223) | 115 (50–180) |

Pancreases were divided in four parts and cultured for 6 days in either control or experimental media. Tissue weight refers to the original weight before culture and DNA content to the final content after culture. Absolute values are shown for the controls; effects of growth factors are expressed as percent of each individual control (mean and 95% CI).
†cultured in 1% human serum (all other growth factors used in 10% serum).
*p < 0.05; p < 0.01; *p < 0.001, as compared with the hypothesized population mean (= 100) with the two-tailed one sample t test.

slightly, but significantly, lower in 1% HSA (9.2 vs. 13.4 ICC/mg, Table 1).

EXAMPLE 2

Effect of Growth Factors on Yield of ICCs

The growth factors having a stimulating effect on the ICC yield included HGF/SF, IGF-II, FGF-2 and FGF-7 at the concentrations shown in Table 1. The effects of TGF-α, EGF, NGF, IGF-I and PDGF were not significant. TGF-β had a potent inhibitory effect, unlike any other factors tested (Table 1). This potential problem can be obviated by adding an anti-TGF-β antibody to the culture medium.

The most potent stimulatory growth factor was HGF/SF (about 3-fold increase in ICC number). The ICCs formed in the presence of HGF/SF were generally more translucent and rounded than controls.

Although FGF-2 was nearly as potent a stimulator of ICC formation as HGF/SF (about a 2.6-fold increase), this appeared to induce the formation of two different types of ICCs: small translucent ones (shown by immunostaining to be mostly epithelial), and larger, more dense clusters containing primarily non-epithelial cells. FGF-7 was least effective.

EXAMPLE 3

Effects of Growth Factors on Insulin Content

Insulin was measured by a commercial solid phase RIA kit after 16 hr acid ethanol extraction at +4° C. The assay CV was 8.3 and 12.2% for control samples containing 136 and 28 μU/ml insulin, respectively.

Most of the growth factors tested were without effect on total insulin content of the cells. HGF/SF, FGF-2 and IGF-I were the only factors that increased the total content of insulin in this respect. HGF/SF clearly is the most potent, causing a 180% increase. A fundamental difference between HGF/SF and FGF-2 was observed; the latter actually decreased the average insulin content per unit DNA by 30%, whereas the former induced a 65% increase in the same parameter (Table 1, FIG. 1). FGF-7 caused an even stronger decrease in the insulin content per DNA than did FGF-2.

The total insulin content was not affected by TGF-β, but, as the result of dramatic decrease in total DNA caused by this factor, the insulin content per DNA was increased by 3.6 fold (Table 2, FIG. 1).

EXAMPLE 4

Effects of Antibodies

As expected, the neutralizing TGF-β antibody had an effect opposite that of the antigen itself, suggesting that either the ICCs or serum-containing medium may have been a source of TGF-β. The ICC yield was increased and DNA synthesis stimulated by the TGF-β antibody. There was also a 61% increase in the total insulin content (Table 2).

TABLE 2

Effect of polyclonal TGF-β antibody and monoclonal IGF-I receptor antibody on the development of ICCs, DNA synthesis and insulin content after 5 days of culture.

|  | anti-IGF-R (n = 3) | anti-TGF-β (n = 5) |
|---|---|---|
| ICC yield per mg tissue | 64(32–86)* | 183(145–221)** |
| DNA content per mg tissue | 82(6–169) | 196(62–330) |
| $^3$H-Thymidine incorporation |  |  |
| per mg tissue | 70(0–161) | 173(101–251)* |
| per DNA | 84(25–141) | 96(66–124) |
| Insulin content |  |  |
| per mg tissue | 89(0–239) | 161(99–224) |
| per DNA | 107(0–217) | 106(17–194) |

Data are expressed as percent of control ICCs originating from the same pancreas and cultured without added antibody in medium containing 10% HS (mean and 95% CI).
*, **, $p < 0.05, 0.01$; one group t-test (population mean = 100)

In order to test whether the relatively weak effects of exogenous IGFs were due to the presence of endogenous IGFs, the IGF-1 receptor was blocked with a neutralizing antibody. In contrast to the effect of the TGF-β antibody, there was a significant (36%) decrease in the number of ICCs, whereas DNA synthesis and insulin levels were not affected (Table 2).

EXAMPLE 5

Morphometry

The three most potent growth factors (HGF/SF, FGF-2 and TGF-β) were studied for their effects on the cell populations contained within the ICCs. Based on the epithelial cell content after 7 days in culture, it was apparent that only HGF/SF had stimulated the growth of epithelial cells. In contrast, the proportion of epithelial cells was 50% lower after culture with either FGF-2 or TGF-β (Table 3). Together with the data presented above, this implies that FGF-2 mainly stimulated the growth of non-epithelial cells, and that the growth-inhibitory action of TGF-β was primarily targeted on epithelial cells. In the FGF-2-treated cultures, the non-epithelial cells were mainly found in large (>100 μm) rounded cell clusters consisting of relatively small cells, whereas in the TGF-β-treated cultures the non-epithelial cells were often seen centrally in irregularly shaped cell clusters with epithelial and insulin-positive cells in the periphery.

In the control cultures, insulin staining was usually found in single cells or in small groups of positive cells scattered within the ICCs; occasionally, however, the staining was seen in cell groups appearing to bud out of the ICC. These insulin-positive outgrowths were more commonly encountered in the HGF/SF-treated ICCs. Insulin-positive cells accounted for 4% of the total cell surface area in sections of the control ICCs. FGF-2- and TGF-β-treated ICCs did not differ from the controls, whereas the insulin-positive area of HGF/SF-treated ICCs was 2.3-fold higher (9.4% vs. 4.0%, p<0.01; Table 3).

The mean cell size was not different in HGF/SF-treated and control ICCs (62.1 vs. 69.3 μm$^2$, respectively). As only less than 10% of these cells represented β-cells, the sizes of individual insulin-positive cells were also measured. The mean size of insulin-positive cells was 1.6-fold higher than the average cell size. Again, there were no differences between HGF/SF-treated and control cells (110 vs. 108 μm$^2$, respectively).

BrdU labeling of FGF-2-treated ICCs was almost twice as high as that of controls (6.9 vs. 3.7%, p<0.05, Table 3). The labeling of HGF/SF-treated ICCs was nearly as high as after FGF-2 treatment (6.3%). The Labeling Index of TGF-β-treated ICCs was significantly lower (1.9%, p<0.05) confirming the results obtained with $^3$H-thymidine incorporation. Cells positive for both insulin and BrdU were scarce, accounting for only 2.5% of all BrdU-labelled cells in control cultures. HGF/SF markedly increased the BrdU labeling of insulin-positive cells (7.4% of all labelled cells, p<0.01, Table 3, FIG. 2).

TABLE 3

Morphometric analysis of cell populations in the ICCs after 6 days of culture with growth factors.

|  | Control | HGF/SF | FGF-2 | TGF-β |
|---|---|---|---|---|
| Epithelial cells (% of surface area) | 55.7 ± 2.0 | 64.5 ± 2.8 | 28.3 ± 2.1* | 38.6 ± 8.1* |
| Insulin cells (% of surface area) | 4.04 ± 0.73 | 9.38 ± 1.14* | 3.39 ± 0.78 | 6.05 ± 1.04 |
| BrdU labeling index (%) | 3.68 ± 0.53 | 6.34 ± 1.31 | 6.85 ± 0.96* | 1.88 ± 0.29 |
| Insulin + BrdU double positive cells of total BrdU cells | 10 of 408 (2.45%) | 27 of 363$^\#$ (7.44%) | 11 of 597 (1.84%) | 1 of 114 (0.88%) |

Values are the means ± S.E.M. of 4 separate experiments, except for insulin/BrdU double positive cells, which are expresed as total numbers of nuclei detected in the 4 sections.
Significant differences between groups are indicated as follows:
*p < 0.05, as compared with control (Fisher's PLSD test after one-way analysis of variance)
$^\#$p < 0.01, as compared with control (Chi-square test)

EXAMPLE 6

Use of HGF/SF to Increase Transplantable Human Fetal Islet Tissues

HGF/SF- or FGF-2-induced ICCs (500), produced as in the preceding examples, and 500 control ICCs were transplanted under the kidney capsule of athymic nude mice. The treated clusters developed into functional islet tissue, as judged by human C-peptide response to a glucose challenge (HGF/SF, 5.0-fold increase; FGF-2, 1.9-fold increase, both relative to the controls. However, the absolute level and response of the serum C-peptide was significantly (p<0.01) lower with FGF-2-treated grafts, whereas HGF/SF-treated grafts were functionally and morphologically identical with normal controls.

Thus, HGF/SF pretreatment of human fetal pancreatic cells intended for transplantation results in significant increases in the transplantable cell mass.

Accordingly, among the peptide growth factors screened for their mitogenic, morphogenic and insulinotropic action in cultures consisting of mixed human fetal pancreatic cells, it was found that HGF/SF is the most potent stimulus for ICC formation from fetal pancreatic cells, and, most importantly, that HGF/SF is the only factor that increases the epithelial, β-cell and insulin content of the cells. The BrdU experiments confirmed the mitogenic effect of HGF/SF on β-cells or their precursors. By contrast, TGF-β has an endogenous anti-proliferative effect on pancreatic epithelial cells.

These data establish that HGF/SF is useful in generating a more-abundant and more-differentiated source of islet cells or their precursors for use in treating a patient with Type 1 diabetes mellitus by islet cell transplantation. In a typical procedure, primary cultures of human fetal pancreatic cells are contacted with HGF/SF, without or with anti-TGF-β human or humanized antibodies, under conditions such that the β-cells in such cultures proliferate and differentiate into insulin-producing islet cell clusters containing a large proportion (e.g., 50%) of β-epithelial cells, and the cultures then administered to the patient parenterally, for example, by an intraportal, intrasplenic, renal subcapsular or intravenous route.

EXAMPLE 7

Ex vivo Expansion of Human Fetal Pancreatic Cells by Growth on 804G Extracellular Matrix in the Presence of HGF/SF The human fetal pancreases (HFP) were provided by Anatomic Gift Foundation (Laurel, Md.) and Advanced Bioscience Resources (Oakland Calif.), both non-profit institutions. Informed consent for tissue donation was obtained by the procurement centers and our IRB reviewed and approved the use of fetal tissues for these studies.

Isolation of ICCs. Pancreases were obtained after the termination of pregnancy by dilatation and extraction between 18 and 24 weeks of gestation. Gestational age was determined by several criteria including bi-parietal diameter, femur length and fetal foot measurement. Warm ischemic time was approximately 5 min and cold ischemic time approximately 24 hours. Tissue was digested as previously described {906} and the fragments incubated in petri dishes that do not allow attachment in RPMI-1640 medium containing 10% pooled human serum, and antibiotics (100 U/ml penicillin, 0.1 mg/ml streptomycin, and 1 μg/ml amphotericin b). Hepatocyte growth factor/scatter factor (HGF/SF) was added to the cultures at 10 ng/ml concentration.

Expansion of cells from ICCs in monolayers. After 2 days culture in petri dishes, monolayers were derived from ICCs according to protocols previously published by us for rodent (Hayek et al. 1989, above) and human pancreatic cells (Beattie et al., *J. Clin. Endocrinol. Metab.*, 78:1232 (1994)). Matrices used were BCEM or 804G and were prepared according to Hayek et al. 1989, above. Selected ICCs of uniform size (50–70 μm diameter) and homogeneous translucent appearance were hand-picked and plated in RPMI-1640 containing 10% human serum on tissue culture dishes alone, or coated with either 804G or BCEM matrix. ICCs selected in this way are highly enriched for epithelial cells. Control ICCs were allowed to remain free floating in petri dishes. In some dishes HGF/SF was added at varying concentrations.

Quantitation of cell number. Single cell suspensions of ICCs were made by incubating in dissociating medium in a 37° C. water bath shaking at 30 cycles/min. After 15 min intervals, cells were dispersed by titurating several times with a pasteur pipette. Single cells were removed by aspiration and kept on ice after allowing clumps to settle in the tube. This process was repeated till no clumps remained. Cells were also removed from matrices using dissociating medium prior to counting in a hemocytometer. Cells were counted from quadruplicate dishes in 3 separate experiments. To estimate number of cells/ICC of starting material, single cell suspensions of 100 ICCs from 10 different isolations were quantitated.

Immunocytochemistry. Monolayers or reaggregated ICCs were fixed in 4% paraformaldehyde and 5 μ sequential sections were stained using hematoxylin and eosin and the immunoalkaline phosphatase technique, using guinea pig anti-porcine insulin (Chemicon, El Segundo, Calif.) or the mouse mAb to human epithelial antigen Ber-EP4 (DAKO, Carpinteria Calif.) were used as the primary antibody. Normal rabbit or mouse serum were used as control sera. Quantitation of the immunostaining was accomplished using a computerized image analysis system (Oncor, San Diego, Calif.). At least 1200 cells were examined in each of 5 different samples, and the data were expressed as percent of surface area ±SE. The person doing the morphological analysis was blinded from the identity of the samples. Acid β-galactosidase (β-gal) activity was localized with a 4 hr incubation using X-gal as the substrate at acidic pH; this enzyme is considered a marker of pancreatic islet cells.

Hormone assays. Insulin was measured using a solid phase RIA assay kit, (Diagnostic Products, Los Angeles, Calif.). Insulin was extracted from tissues using acid ethanol according to standard techniques. The data were quantified by fluorescent measurement of DNA of each sample.

RNA6e protection assays. RNA protection assays were performed as previously reported (Beattie et al. 1994, above).

Statistical analyses. Where necessary, data was analyzed with software for the MacIntosh (Statview IV; Abacus Concepts, Berkeley, Calif., USA). Statistical significances of observed differences was tested using ANOVA and Fischer's protected least significance difference test using 95% level as the limit of significance.

Transplantation studies. After the different tissue culture treatments, cells were transplanted under the kidney capsule of athymic nude mice as described above. 500 ICCs or 250,000 monolayer cells; equivalent to 500 ICCs, or 500 reaggregated ICCs were transplanted. After 3 months the animals were challenged with 3 g/Kg glucose and serum human C-peptide measured by RIA.

Figure 3:
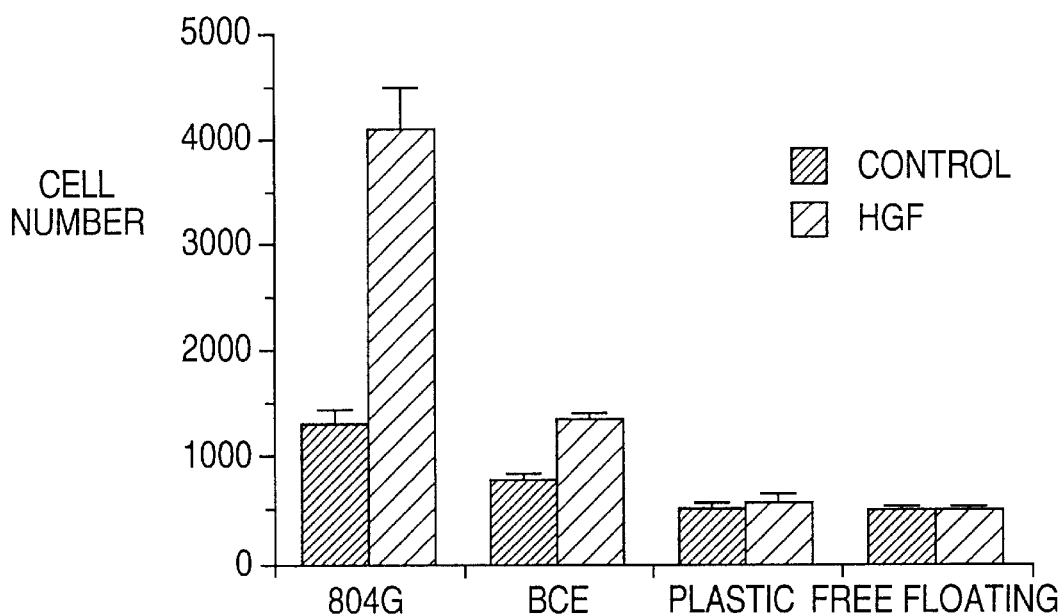
FIG. 3 shows the effect of extracellular matrices 804G and BCE on the mitogenic effect of HGF/SF in fetal human pancreatic cells as reflected in cell number.
Figure 4:
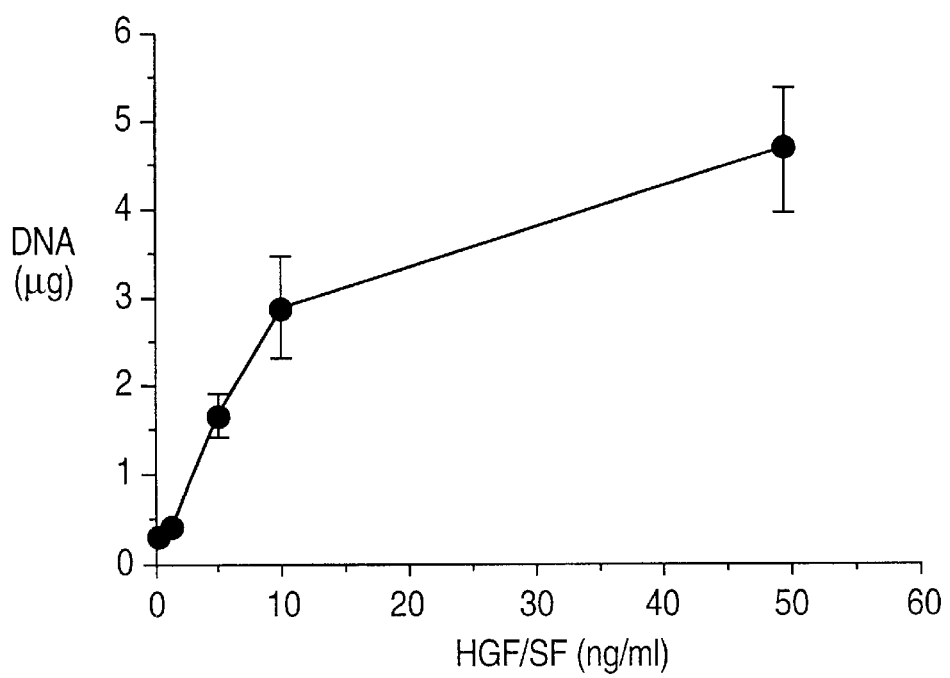
FIG. 4 shows that the mitogenic effect of HGF/SF is dose dependent.
Figure 5:
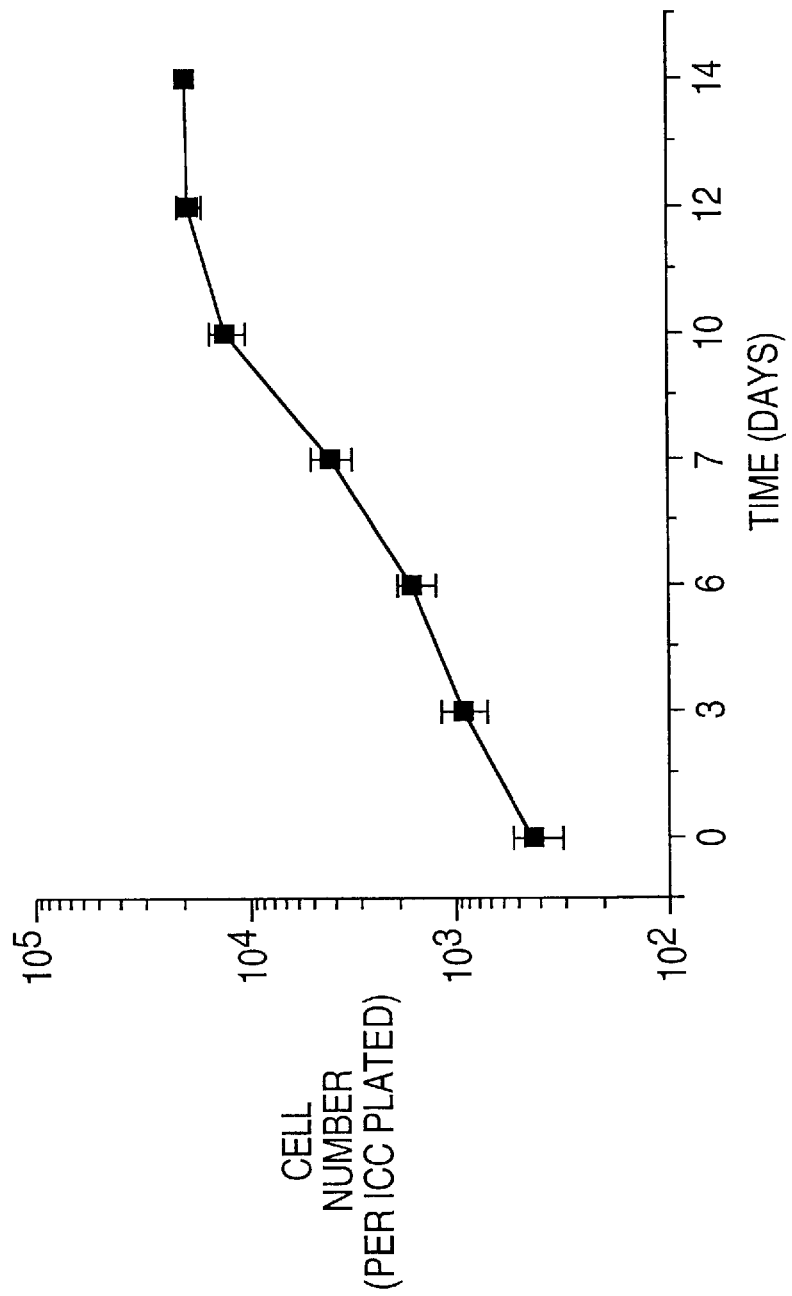
FIG. 5 shows the cell doubling time in the presence of HGF/SF.
Figure 6A:
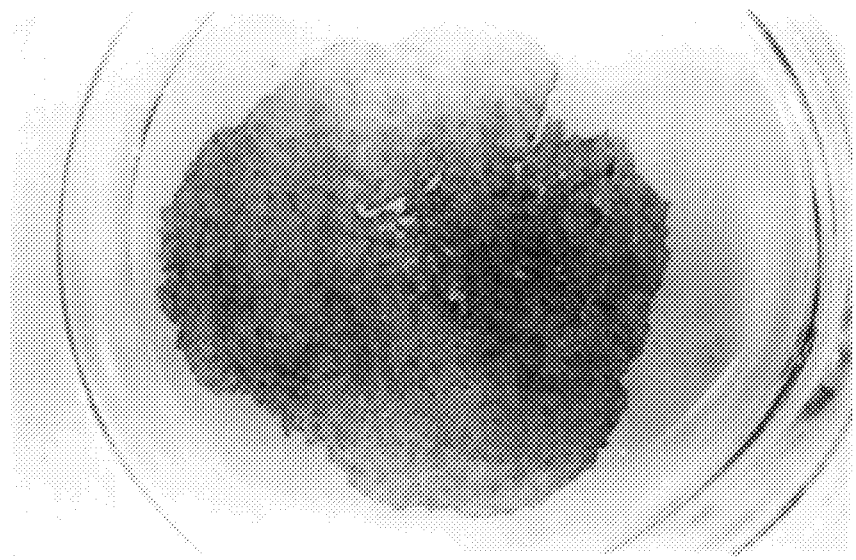
FIGS. 6A and 6B show expansion of monolayers due to HGF/SF that result from a combination of increased proliferation and cell spreading (6A, control; 6A, HGF/SF).
Figure 6B:
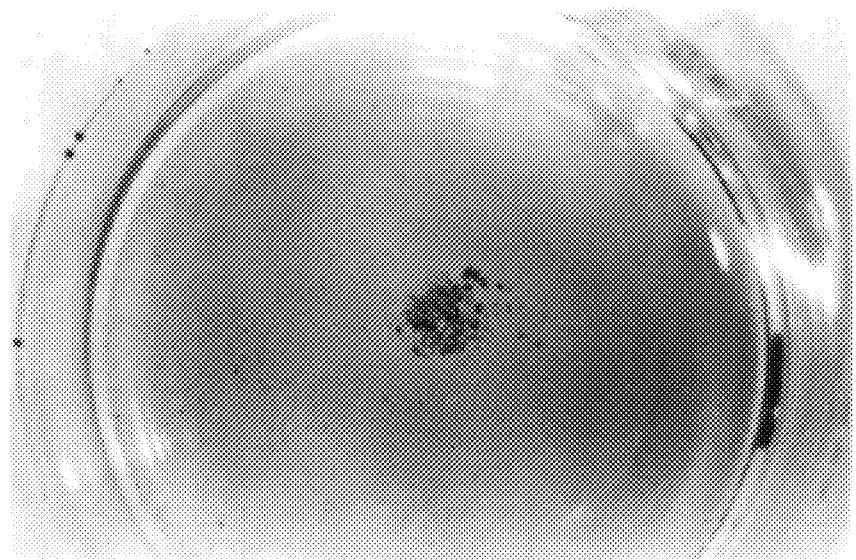

When human fetal pancreas digests were grown free floating in petri dishes in the presence of HGF/SF there was a 2–3 fold increase in the number of ICCs generated compared to growth in the absence of HGF/SF. Moreover, these ICCs had increased epithelial and fl-cell content. Handpicking of uniform ICCs (50–70 μm diameter, approximately 400 cells/ICC) of translucent, homogeneous appearance further augmented the epithelial content. After plating on dishes coated with either 804G or BCEM matrix ICCs attached overnight and monolayer formation was generally initiated by 24 hours. On uncoated tissue culture dishes attachment and monolayer formation were poor. After one week cell numbers increased 10-fold in the presence of HGF/SF and 804G matrix compared to ICCs grown in the absence of matrix or growth factor. A 3-fold increase was observed in ICCs plated on 804g alone compared to no matrix; a 2-fold increase compared to BCEM alone. There was no mitogenic effect of HGF/SF observed in the absence of matrix (FIG. 3). The mitogenic effect of HGF/SF was dose dependent (FIG. 4), and cell doubling time was 46 hours at a concentration of 10 ng/ml (FIG. 5). Under the influence of the growth factor, cell spreading was observed, as evidenced by a 2.5-fold increase in size of monlayer compared to cell number (FIG. 6).

Transcription of the insulin and glucagon genes is down-regulated in actively proliferating cells in monolayer culture on a matrix. Immunostaining of monolayers after growth on 804G matrix in the presence of HGF/SF demonstrated that the expanded cell population was comprised of virtually all epithelial cells which were positive for acid β-gal (a marker for endocrine precursor cells), with only rare cells staining for insulin. This is quantified in FIG. 7. Under conditions in which the production of a control, uninvolved epthelial antigen, EP4, was similar in all experimental conditions tested (FIG. 7, bottom), the amount of insulin was very low in untreated monolayers ("MONOLAYER"), but many-fold greater when such monolayer cells were reaggregated and treated with nicotinamide ("REAGG+NIC").

Figure 8:
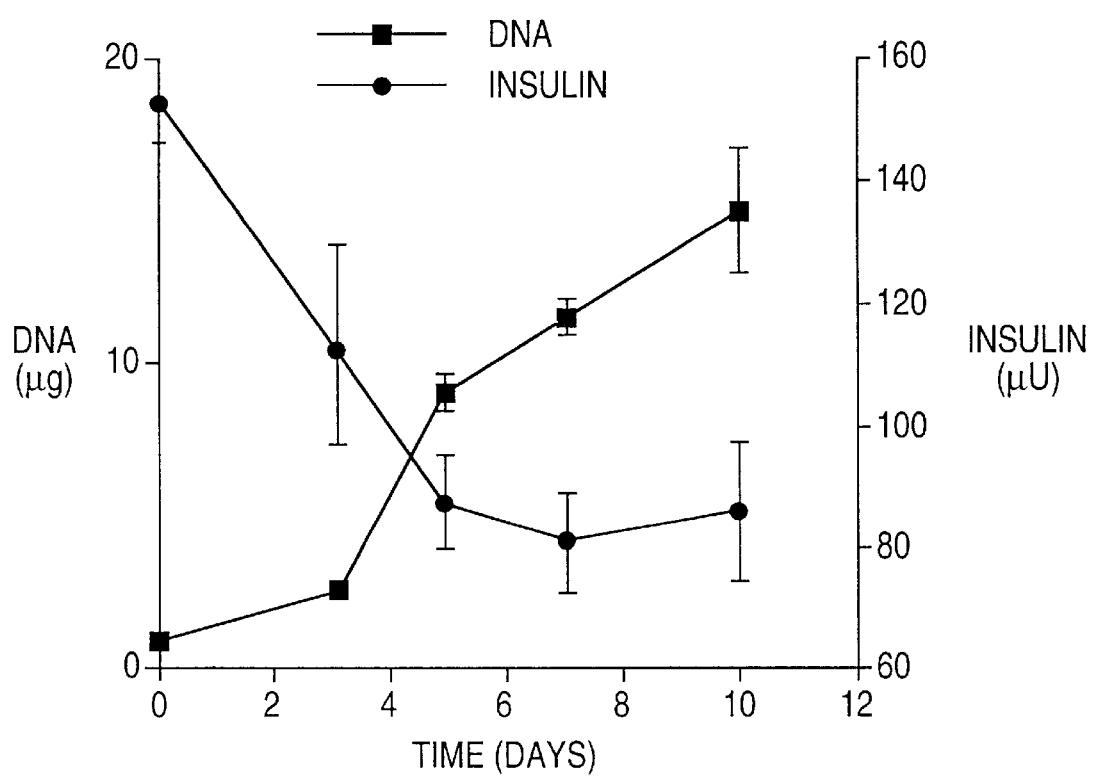
FIG. 8 shows inverse relationship between DNA and insulin content as the cell population expanded in monolayer on extracellular matrix.

As the cell population expanded in monolayer over the course of 10 days there was a reverse correlation between DNA and insulin content (FIG. 8). Transcriptional analysis by RNAse protection assay showed that after normalizing to the cyclophilin signal, the expression of glucagon and insulin mRNAs in monolayers was decreased significantly over a 10 day period, compared to that in ICCs that had remained free floating. This down regulation of hormone genes was partially reversed by reaggregation of the cell population, and could be further increased by the presence of nicotinamide, as described below.

EXAMPLE 8

Reaggregation of Monolayer Cells

After 5 days of monolayer growth, cells were removed from the matrix using non-enzymatic dissociating medium (Sigma Corp., St. Louis, Mo.). After dispersing and washing in medium, single cell suspensions were reaggregated as previously described. Rouller et al., *Exp. Cell Res.* 191:305 (1990). Briefly, cells were placed in media in cryovials (Nalge Co., Rochester, N.Y.), placed in a 37° C. water bath at a 45° angle and shaken for 1 hr at 70 cycles/ min. Thereafter, cell aggregates were transferred to petri dishes. Nicotinamide (NIC; Sigma Corp., St Louis, Mo.) at 10 mM was added to some dishes. Control dishes included both ICCs that had remained free floating in petri dishes throughout the course of the experiment, and monolayers of ICCs that had not been reaggregated.

Figure 7A:
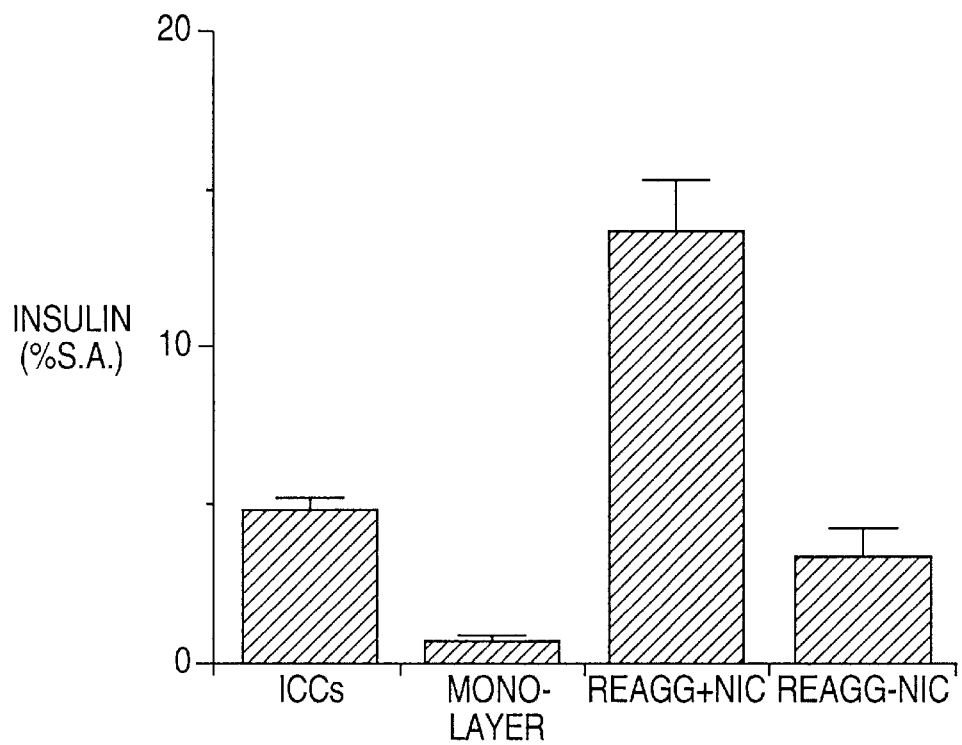
FIGS. 7A and 7B show the quantitation of the surface area of cells immunostained for insulin and EP4 (an epithelial antigen that is a marker for pancreatic epithelial cells) in ICCs and in ICCs reaggregated without and with nicotinamide.
Figure 7B:
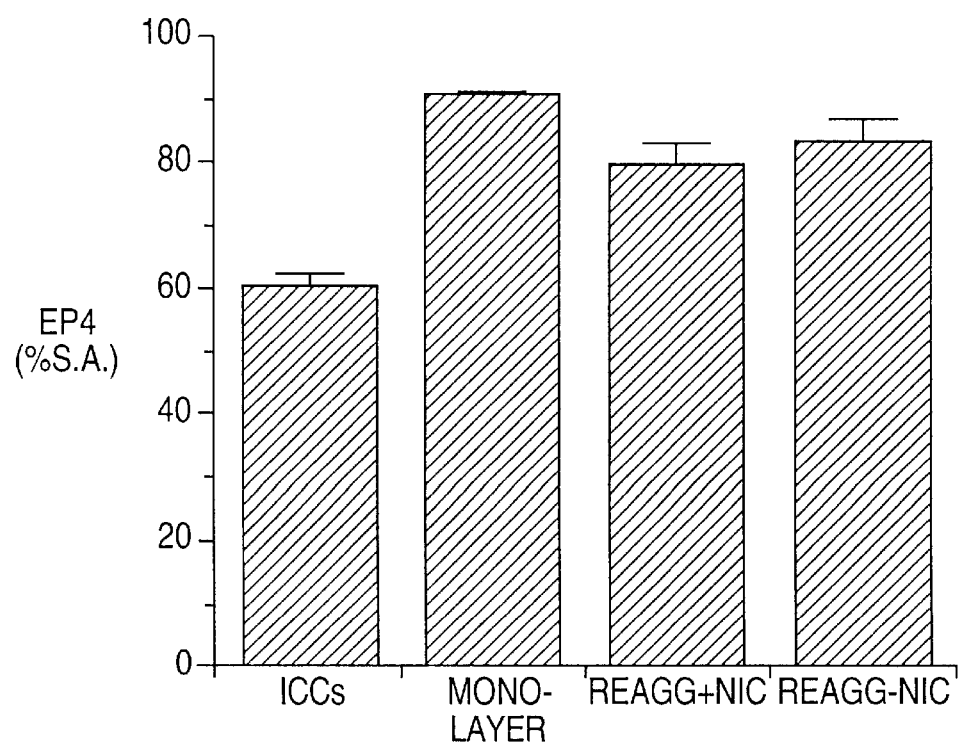
Figure 9:
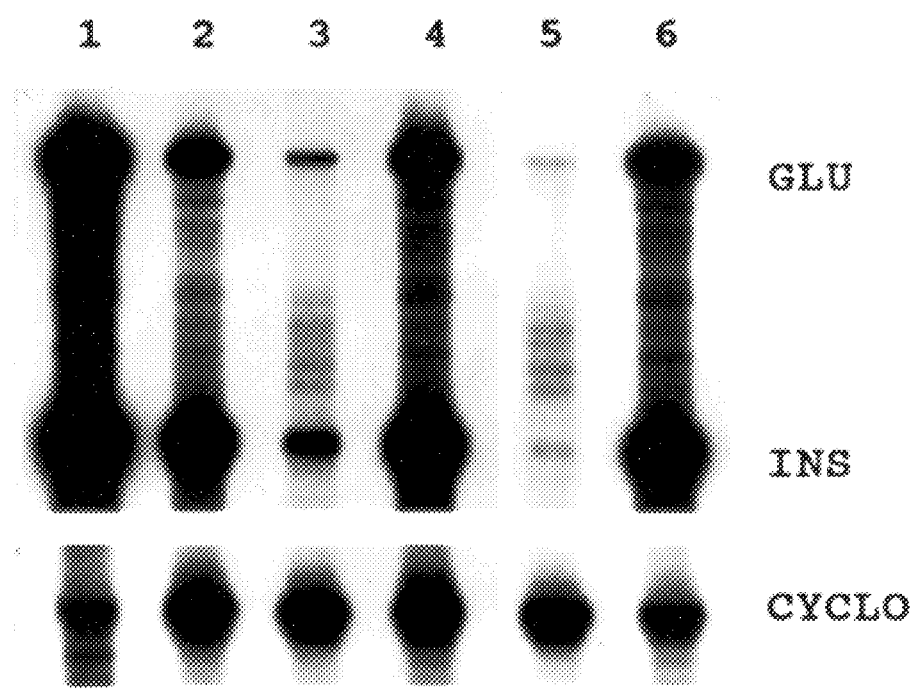
FIG. 9 shows a ribonuclease protection assay of transcriptional levels of glucagon, insulin and cyclophilin.
Figure 10:
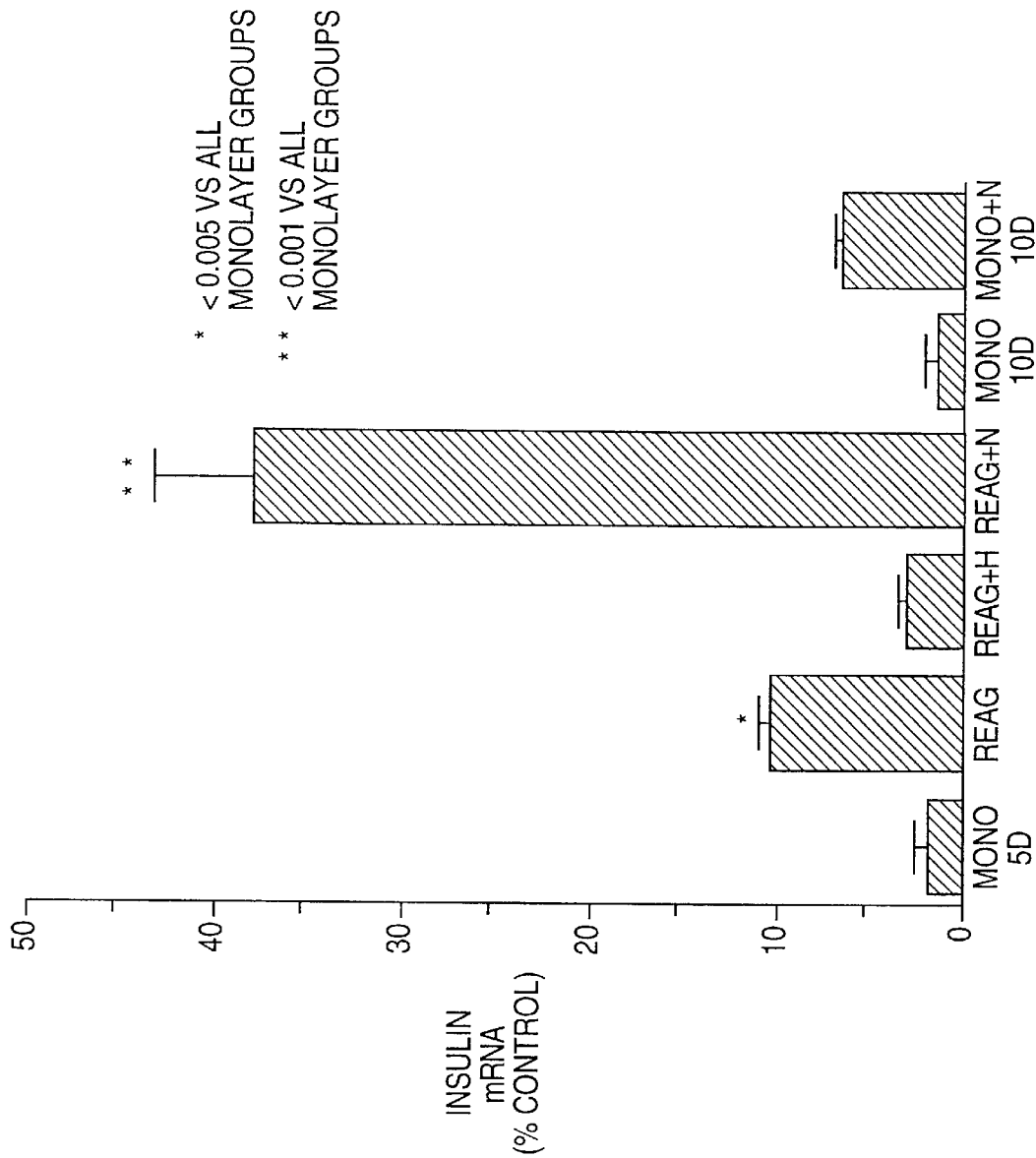
FIG. 10 shows the levels of insulin mRNAs in cells in the presence of nicotinamide.

Islet-specific gene transcription was upregulated by cell reaggregation of expanded monolayers. When cells from expanded monolayers were reaggregated to form ICCs and incubated, free floating, in petri dishes for 5 days, levels of expression of insulin and glucagon mRNAs increased significantly compared to those of the cells in monolayer. This effect was potentiated by the addition of 10 mM nicotinamide to the free floating aggregates (FIGS. 7, 9, and 10). Immunohistochemical analysis of reaggregated ICCs cultured for 5 days in the presence of nicotinamide demonstrated well-formed ICCs with a significantly greater surface area of insulin containing cells than in reaggregates cultured in the absence of nicotinamide.

Figure 11:
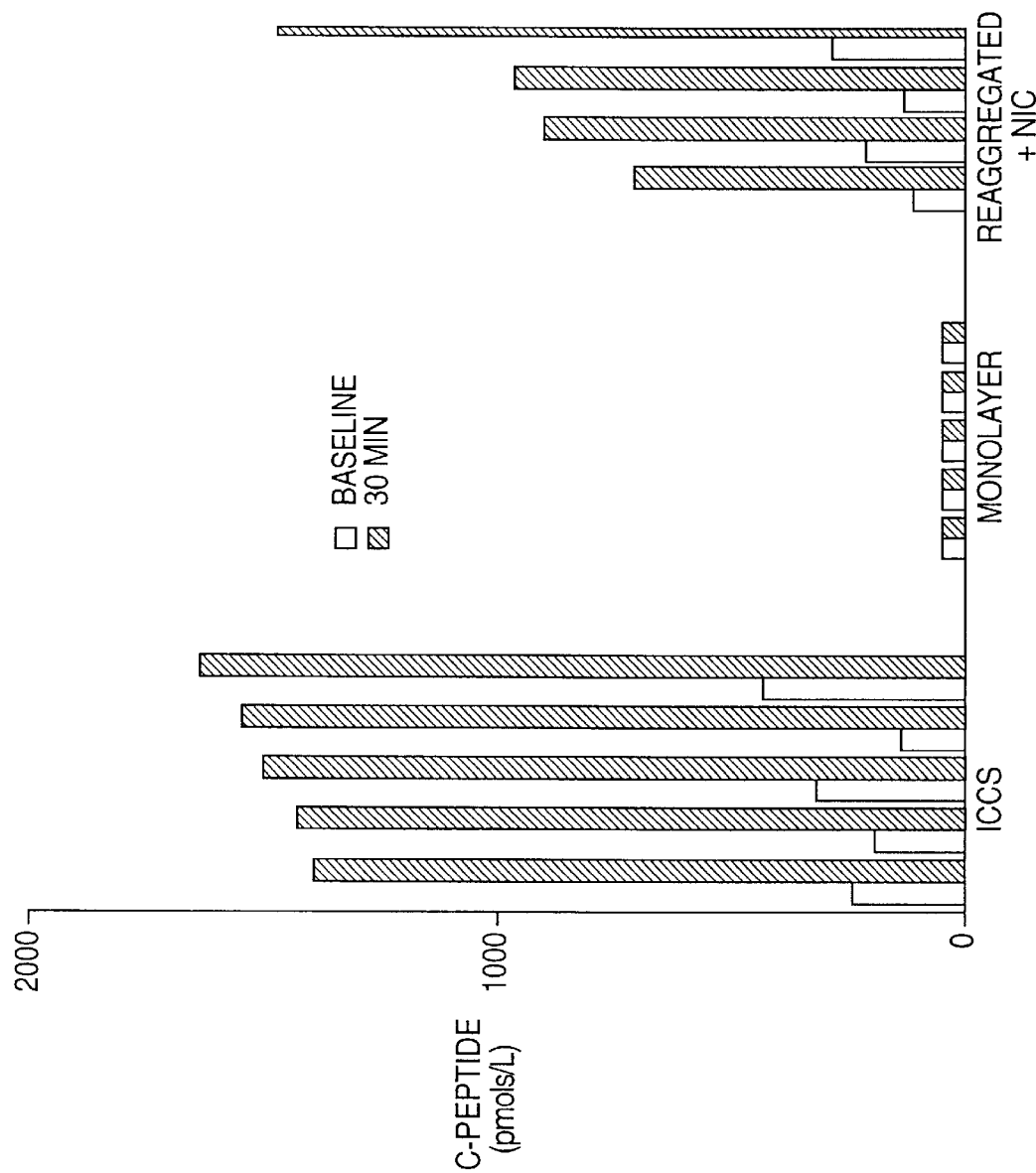
FIG. 11 shows the glucose-induced release of human insulin C-peptide in athymic nude mice following transplantation into nude mice and maturation of various human fetal pancreatic cell preparations. ICCs=positive control, transplanted fresh ICCs. Monolayer=transplanted cells from monolayers on grown on 804G. Reaggregated+NIC=cells from monolayers reaggregated, treated with nicotinamide, and then transplanted.

The transplantation data is depicted in FIG. 11. Only the grafts in those athymic nude mice that received transplants of reaggregated cells were able to respond to a glucose challenge as evidenced by an increase in circulating human insulin C-peptide.

EXAMPLE 9

Effects of HGF/SF and Matrix 804G on Proliferation of Adult Human Pancreatic Cells Adult human pancreatic islets (90% pure by DTZ, 20 islets per well, about 15,000 cells per well) were cultured on 804G matrix in the absence and presence of HGF/SF (10 ng/ml) in RPMI-1640 medium with 5.5 mM glucose. After one week, cell counts were determined.

| Control | + HGF/SF |
|---------|----------|
| 14,000  | 21,000   |
| 14,000  | 23,000   |
| 19,000  | 23,000   |

It is clear from these experiments that adult human pancreatic epithelial cells will proliferate in monolayer on a matrix following exposure to the cytokine. The effect is not, however, nearly as profound as in fetal pancreatic cells.

What is claimed is:

1. A method for stimulating the ex vivo proliferation of human adult pancreatic β-islet cells, comprising the steps of:
   (a) preparing a primary culture of human adult pancreatic cells; and,
   (b) contacting said primary culture cells with an effective concentration of HGF/SF, wherein the effective concentration is an amount sufficient to induce the primary culture to proliferate.

2. A method of claim 1, further comprising contacting said primary culture cells with an effective concentration of anti-TGF-β-antibodies, wherein the effective concentration is an amount sufficient to increase cell proliferation.

3. A method of claim 1, wherein said cell proliferation comprises an increase in β-epithelial cell number relative to other cell types.

4. A method of claim 1, wherein said cell proliferation comprises an increase in average cellular insulin production.

5. A method of claim 1, wherein said effective concentration of HGF/SF ranges from about 5 to about 50 ng/ml.

6. A method of claim 1, further comprising growing said cultured cells in monolayer on an extracellular matrix in the presence of said HGF/SF.

7. A method of claim 6, wherein said extracellular matrix is the 804G extracellular matrix.

8. A method of claim 6, wherein said extracellular matrix is the BCEM extracellular matrix.

9. A method of claim 6, further comprising reaggregating said monolayer culture cells.

10. A method of any one of claims 1, 6 or 9, further comprising contacting said cells with an agent that upregulates the insulin gene.

11. A method of claim 10, wherein said agent is an poly (ADP-ribose) synthetase inhibitor.

12. A method of claim 11 wherein said inhibitor is a nicotinamide or a benzamide.

13. A method for stimulating the ex vivo proliferation of human adult pancreatic β-cells, comprising the steps of:
   (a) preparing a primary culture of human adult pancreatic cells;
   (b) culturing said cells with an effective concentration of HGF/SF, wherein the effective concentration is an amount sufficient to induce the primary culture to proliferate, under conditions such that islet cell clusters form;
   (c) culturing said clusters as a monolayer on an extracellular matrix in the presence of the effective concentration of HGF/SF;
   (d) dissociating said cells from said monolayer by non-enzymatic means; and,
   (e) reaggregating said dissociated cells in the presence of an inhibitor of poly (ADP-ribose) synthetase, thereby stimulating the ex vivo proliferation and differentiation of human fetal pancreatic β-cells.

14. A method for treating a subject with Type 1 diabetes mellitus, comprising the steps of:
(a) preparing a primary culture of human adult pancreatic cells;
(b) contacting said primary culture with a reagent comprising an effective concentration of HGF/SF, wherein the effective concentration is an amount sufficient to induce the primary culture to proliferate, so as to produce from said cultures increased numbers of insulin-producing, islet-like cell clusters containing β-epithelial cells;
(c) harvesting the thus-treated adult pancreatic cells; and,
(d) parenterally transplanting in said subject an effective amount of said cells of part (c) above.

15. A method of claim 14, wherein said parenterally transplanting comprises administering by an intraportal, intrasplenic, renal subcapsular route, or intravenous route.

16. A method of claim 14, wherein step b) further comprises growing said cells in monolayer culture on an extracellular matrix in the presence of an effective concentration of HGF/SF.

17. A method of claim 16, wherein said extracellular matrix is 804G or BCEM.

18. A method of claim 16, further comprising dissociating by non-enzymatic means said monolayer cells from said matrix, then reaggregating said dissociated cells.

19. A method of claim 18, further comprising contacting said reaggregated cells with an agent that upregulates the insulin gene in said cells.

20. A method of claim 19, wherein said agent is a poly(ADP-ribose) synthetase inhibitor.

21. A method of claim 20 wherein said inhibitor is a nicotinamide or a benzamide.

22. The method of claim 14, further comprising contacting the primary culture with an amount of anti-TGF-β antibody sufficient to further induce the primary culture to proliferate.

23. A method of producing proliferating and differentiating human adult pancreatic islet cells in clinically useful quantities, comprising the steps of:
(a) seeding a bioreactor with a human pancreatic cell culture;
(b) perfusing said bioreactor with a complete growth medium supplemented with an amount of HGF/SF sufficient to induce the cells to proliferate and differentiate; and
(c) harvesting islet-like cell clusters containing β-epithelial cells from said bioreactor.

24. A method of claim 23, further comprising the steps of:
(a) seeding said clusters into a second bioreactor whose growing surface is coated with an extracellular matrix;
(b) perfusing through said second bioreactor a growth medium supplemented with an effective concentration of HGF/SF, and optionally with an effective concentration of anti-TGF-β antibody;
(c) dissociating cells from said matrix by non-enzymatic means;
(d) reaggregating said disssociated cells; and, (e) contacting said reaggregated cells with an insulin gene upregulating agent.

25. The method of claim 23, further comprising contacting the primary culture with an amount of anti-TGF-β antibody sufficient to further induce the cells to proliferate and differentiate.

* * * * *